United States Patent
Sugahara

(10) Patent No.: US 12,150,795 B2
(45) Date of Patent: Nov. 26, 2024

(54) MEDICAL IMAGING SYSTEM AND MEDICAL IMAGING PROCESSING APPARATUS

(71) Applicant: FUJIFILM Corporation, Tokyo (JP)

(72) Inventor: Masataka Sugahara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 269 days.

(21) Appl. No.: 17/586,697

(22) Filed: Jan. 27, 2022

(65) Prior Publication Data

US 2022/0151573 A1 May 19, 2022

Related U.S. Application Data

(63) Continuation of application No. PCT/JP2020/027395, filed on Jul. 14, 2020.

(30) Foreign Application Priority Data

Jul. 29, 2019 (JP) ................. 2019-138506

(51) Int. Cl.
*A61B 6/04* (2006.01)
*A61B 6/00* (2024.01)
*A61B 6/46* (2024.01)
*G06T 7/70* (2017.01)

(52) U.S. Cl.
CPC ............... *A61B 6/04* (2013.01); *A61B 6/466* (2013.01); *A61B 6/5229* (2013.01); *G06T 7/70* (2017.01)

(58) Field of Classification Search
CPC ......... A61B 6/04; A61B 6/466; A61B 6/5229; A61B 6/08; A61B 6/0407; A61B 6/505; A61B 6/40; A61B 6/0421; A61B 6/4021; A61B 6/44; A61B 6/4429; A61B 6/4452; A61B 6/5205; A61B 6/5211
See application file for complete search history.

(56) References Cited

U.S. PATENT DOCUMENTS 11,020,068 B2 6/2021 Imamura et al.
2019/0046130 A1* 2/2019 Imamura ................ A61B 6/547

FOREIGN PATENT DOCUMENTS

| JP | 2017023326 | 2/2017 |
|----|-----------|--------|
| JP | 2019033830 | 3/2019 |
| WO | 2016184704 | 11/2016 |
| WO | 2018122451 | 7/2018 |

(Continued)

OTHER PUBLICATIONS

"Office Action of Japan Counterpart Application" with English translation thereof, issued on Dec. 27, 2022, p. 1-p. 9.

(Continued)

*Primary Examiner* — David P Porta
*Assistant Examiner* — Casey Bryant
(74) *Attorney, Agent, or Firm* — JCIPRNET

(57) ABSTRACT

A medical imaging system includes an imaging unit that obtains a medical image or data used for generating the medical image by imaging a subject, a processor that stores positioning data for specifying arrangement of the subject with respect to the imaging unit, and a display unit that three-dimensionally displays the arrangement of the subject with respect to the imaging unit by using the positioning data in a case where the subject is imaged using the imaging unit.

11 Claims, 6 Drawing Sheets

(56) References Cited

FOREIGN PATENT DOCUMENTS

WO      WO-2018122451 A1 *   7/2018   ............... A61B 6/03

OTHER PUBLICATIONS

"Office Action of Japan Counterpart Application" with English translation thereof, issued on May 9, 2023, p. 1-p. 12.
"Office Action of Japan Counterpart Application", issued on Aug. 2, 2022, with English translation thereof, p. 1-p. 9.
"Search Report of Europe Counterpart Application", issued on Aug. 10, 2022, p. 1-p. 6.
"International Search Report (Form PCT/ISA/210) of PCT/JP2020/027395," mailed on Oct. 13, 2020, with English translation thereof, pp. 1-5.
"Written Opinion of the International Searching Authority (Form PCT/ISA/237)" of PCT/JP2020/027395, mailed on Oct. 13, 2020, with English translation thereof, pp. 1-8.
"Office Action of Europe Counterpart Application", issued on May 29, 2024, p. 1-p. 3.

* cited by examiner

MEDICAL IMAGING SYSTEM AND MEDICAL IMAGING PROCESSING APPARATUS

CROSS-REFERENCE TO RELATED APPLICATIONS

This application is a Continuation of PCT International Application No. PCT/JP2020/027395 filed on 14 Jul. 2020, which claims priority under 35 U.S.C § 119(a) to Japanese Patent Application No. 2019-138506 filed on 29 Jul. 2019. The above application is hereby expressly incorporated by reference, in its entirety, into the present application.

BACKGROUND OF THE INVENTION

1. Field of the Invention

The present invention relates to a medical imaging system that performs imaging for obtaining a medical image such as a radiation image, and a medical imaging processing apparatus that performs processing related to imaging of the medical image.

2. Description of the Related Art

In the related art, in a medical field, diagnosis and the like using an image obtained by imaging a subject have become widespread. For example, a radiation image obtained by imaging a patient who is a subject using radiation such as X-rays can visualize the inside of the subject non-invasively, and is therefore widely used for diagnosis and the like.

In the diagnosis using the radiation image or the like, it is important to arrange the subject with respect to an imaging unit (for example, a radiographic unit) that captures the radiation image or the like. This is for observing changes over time in the same subject, or for comparison with past cases.

For this reason, in recent years, a medical imaging apparatus that supports positioning of the subject with respect to the imaging unit has been known. For example, in a dental X-ray imaging apparatus that images a dentition or a jawbone, in a case where a face of a subject is optically imaged in a case of X-ray imaging of the dentition, and then X-ray imaging of the dentition is performed for the same subject, the subject can be positioned in the same position as that in the previous imaging by superimposing and displaying a ghost image showing a contour of the face in the case of the previous imaging on a monitor that shows the face part of the subject. There has been known a device that supports such a method (JP2010-148656A).

SUMMARY OF THE INVENTION

In order to support positioning of a subject in capturing a medical image such as a radiation image, for example, there is a method of displaying a position where the subject is to be arranged in an image or a video of the subject or the like.

However, it may not be easy to position the subject with an accuracy required for the radiation image or the like simply by displaying the position where the subject is to be arranged in the image or the video of the subject or the like.

For example, in a case of obtaining a radiation image of a knee joint, the knee joint may move in a complicated manner with respect to a flexion angle, a turning angle with respect to a hip joint, and the like. Therefore, it is necessary to perform imaging by comprehensively and accurately determining not only the overall position (distance) with respect to the imaging unit but also the arrangement related to these plurality of parameters. In this case, in two-dimensional arrangement support display as described above, it is difficult to accurately grasp three-dimensional arrangement of the knee joint related to these plurality of parameters.

In principle, ideal three-dimensional arrangement of the subject can be obtained by performing the two-dimensional arrangement support display in two directions such as front and side surfaces of the knee joint. However, since it is necessary to consider the two-dimensional arrangement support display in two directions in combination, it is still difficult to accurately grasp the three-dimensional arrangement of the knee joint.

Therefore, an object of the present invention is to provide a medical imaging system and a medical imaging processing apparatus capable of supporting more accurate and easy positioning of a subject than in a case of performing two-dimensional arrangement support display of the subject.

A medical imaging system of an aspect of the present invention comprises: an imaging unit that obtains a medical image or data used for generating the medical image by imaging a subject; a processor that stores positioning data for specifying arrangement of the subject with respect to the imaging unit; and a display unit that three-dimensionally displays the arrangement of the subject with respect to the imaging unit by using the positioning data in a case where the subject is imaged using the imaging unit.

It is preferable that the positioning data three-dimensionally specifies a position, a posture, and a shape of the subject.

It is preferable that the positioning data is data relating to the subject, data relating to another subject different from the subject, or schematic model data.

It is preferable that in a case where the positioning data is the data relating to the subject, the positioning data is data representing the arrangement of the subject with respect to the imaging unit in past imaging.

It is preferable that in a case where the positioning data is the data relating to the other subject, the processor stores the positioning data relating to the other subject similar in shape and size to the subject in association with the subject.

It is preferable that the display unit displays the arrangement of the subject in a mode showing a three-dimensional position, posture, and shape of the subject.

It is preferable that the display unit displays the three-dimensional shape of the subject in a mode showing unevenness of the subject.

It is preferable that the processor determines a difference between the subject and the arrangement of the subject displayed by the display unit, and in a case where determination is made that there is the difference, prohibits the imaging unit from imaging the subject.

It is preferable that the processor determines the difference by using a distance, an angle, or a volume between the subject and the arrangement of the subject displayed by the display unit.

It is preferable that the processor detects the subject with respect to the imaging unit from a plurality of locations in a case where the subject is imaged using the imaging unit, and generates the positioning data by using a result of the detection.

A medical imaging processing apparatus of another aspect of the present invention comprises: a processor, in which the processor generates positioning data for specifying arrangement of a subject with respect to an imaging unit that obtains a medical image or data used for generating the medical image, and three-dimensionally displays the arrangement of the subject with respect to the imaging unit on a display unit by using the positioning data in a case where the subject is imaged using the imaging unit.

According to the medical imaging system and the medical imaging processing apparatus of the aspects of the present invention, it is possible to support more accurate and easy positioning of a subject than in a case of performing two-dimensional arrangement support display of the subject.

DESCRIPTION OF THE PREFERRED EMBODIMENTS

First Embodiment

Figure 1:
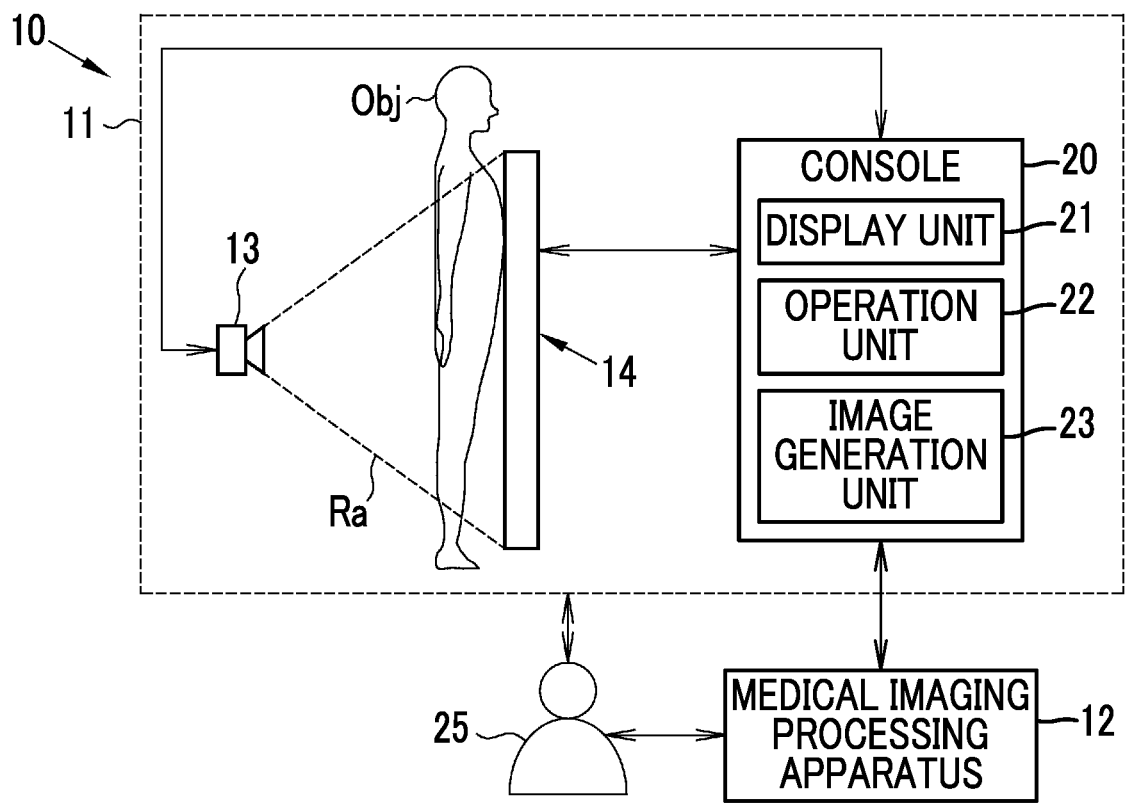
FIG. 1 is a schematic view of a medical imaging system.

As shown in FIG. 1, a medical imaging system 10 comprises an imaging unit 11 and a medical imaging processing apparatus 12.

By imaging a subject Obj, the imaging unit 11 obtains a medical image or data used for generating the medical image (hereinafter, referred to as a medical image or the like). The medical image is an image used for medical observation, examination, and/or diagnosis, and is, for example, a radiation image obtained by imaging the subject Obj using radiation such as X-rays. The data used for generating the medical image is, for example, imaging data used for generating a tomographic image. That is, the data used for generating the medical image is a precursor image or other data acquired to obtain a medical image used for diagnosis or the like in a case where the medical image cannot be directly obtained by simple imaging.

The imaging unit 11 can be configured by using an optional device that obtains the medical image or the like by positioning and imaging the subject Obj. For example, the imaging unit 11 is a radiographic apparatus that images the subject Obj using X-rays or other radiation.

Positioning of the subject Obj means adjusting and positioning a position of the subject Obj with respect to one or a plurality of specific objects (hereinafter, simply referred to as an "imaging unit 11") constituting the imaging unit 11, and includes adjusting a posture of the subject Obj with respect to these objects. The posture of the subject Obj means information regarding an angle for determining a spatial orientation of the whole or a part of the subject Obj, and is information regarding an angle for determining a spatial orientation of a state in which the subject Obj has a specific shape in a case where the whole or a part of the subject Obj can be deformed.

The medical imaging processing apparatus 12 performs processing for providing information relating to the positioning of the subject Obj to a user 25 such as a doctor or a technician who operates the imaging unit 11 in capturing the medical image or the like using the imaging unit 11. As a result, the medical imaging processing apparatus 12 supports the positioning of the subject Obj by the user 25.

In the present embodiment, the imaging unit 11 is a radiographic apparatus that obtains a fluoroscopic image of the subject Obj by imaging the subject Obj using radiation. Therefore, the imaging unit 11 comprises a radiation source 13, a radiographic unit 14, and a console 20.

The radiation source 13 is a device that generates radiation Ra necessary for imaging, and includes a radiation tube for generating the radiation Ra, a high-voltage generation circuit for generating a high voltage required for the radiation tube to generate the radiation Ra, and the like. The radiation source 13 can generate a plurality of types of radiation having different radiation qualities (so-called energy distribution) by adjusting the tube voltage and the tube current of the radiation tube. The energy of the radiation generated by the radiation source 13 is one of imaging conditions. In the present embodiment, the radiation source 13 is an X-ray source that generates X-rays. Therefore, the imaging unit 11 is an X-ray imaging apparatus that acquires an X-ray image of the subject Obj by imaging the subject Obj using X-rays. The subject Obj is, for example, a human body or a part of the human body. The radiation source 13 adjusts the position with respect to the radiographic unit 14 that receives the radiation Ra. This is to obtain an appropriate radiation image that can be used for diagnosis and the like at least with respect to a relative positional relationship between the radiation source 13 and the radiographic unit 14.

The radiographic unit 14 images the subject Obj using the radiation Ra generated by the radiation source 13. Therefore, the radiographic unit 14 has one or a plurality of radiation detection panels for imaging the subject Obj using the radiation Ra. The radiographic unit 14 is a so-called flat panel detector (FPD). Therefore, the radiographic unit 14 outputs a radiation image of the subject Obj by detecting the radiation Ra transmitted through the subject Obj by the radiation detection panel and converting the detected radiation into an electric signal. This radiation image is one of the medical images. In the imaging using the radiographic unit 14, a grid (not shown) can be used in combination as needed. The grid is a device that removes scattered radiation components of radiation, for example, a static type Lysholm blende, a mobile type Bucky blende, or the like. The subject Obj is positioned with respect to the radiographic unit 14. This is to obtain an appropriate radiation image that can be used for diagnosis and the like with respect to the subject Obj or a part of the subject Obj to be imaged.

The console 20 is a control device (computer) that controls operations of the radiation source 13, the radiographic unit 14, and the like, and comprises a display unit 21, an operation unit 22, an image generation unit 23, and the like. The display unit 21 is, for example, a liquid crystal display, and displays a long radiation image or other radiation image captured, and displays other necessary operations or settings. The operation unit 22 is, for example, a keyboard and/or a pointing device used for setting input of the imaging conditions and the like and for operating the radiation source 13 and the radiographic unit 14. The display unit 21 and the operation unit 22 can be constituted by a touch panel. The image generation unit 23 generates a radiation image using the output of the radiographic unit 14.

Figure 2:
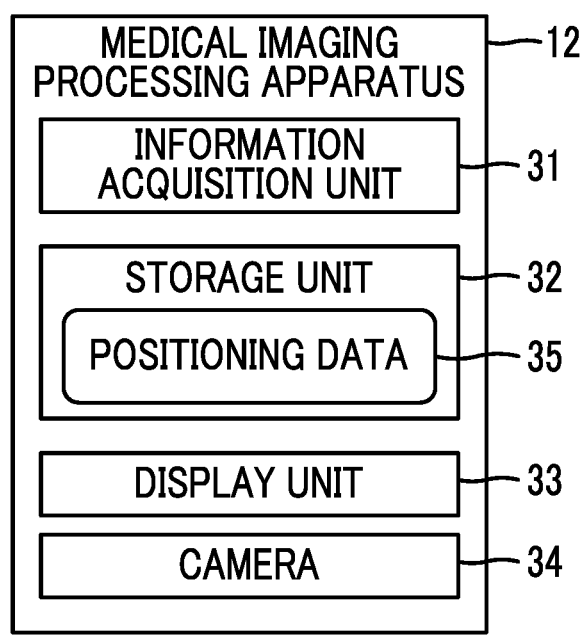
FIG. 2 is a block diagram showing a configuration of a medical imaging processing apparatus.

As shown in FIG. 2, the medical imaging processing apparatus 12 comprises an information acquisition unit 31, a storage unit 32, a display unit 33, and a camera 34. In the medical imaging processing apparatus 12, programs relating to the information acquisition unit 31, the storage unit 32, a determination unit 201 (see FIG. 10), a control unit 202 (see FIG. 10), a subject detection unit 301 (see FIG. 11), a positioning data generation unit 302 (see FIG. 11), and a display control unit 305 (see FIG. 12) are incorporated in a memory (not shown). In a case where the programs are operated by a comprehensive control unit (not shown) composed of a processor, functions of the information acquisition unit 31, the storage unit 32, the determination unit 201 (see FIG. 10), the control unit 202 (see FIG. 10), the subject detection unit 301 (see FIG. 11), the positioning data generation unit 302 (see FIG. 11), and the display control unit 305 (see FIG. 12) are realized.

The information acquisition unit 31 is directly or indirectly connected to, for example, the console 20 to acquire subject information for specifying the subject Obj, such as a name or identifier (ID) and a physique (for example, the size and thickness of an imaging part), and imaging information regarding an imaging part, an imaging direction, and other imaging forms. As a result, the medical imaging processing apparatus 12 cooperates with the imaging unit 11. The term "imaging part" refers to a part of the subject Obj to be imaged, and is, for example, a head, a chest, an abdomen, a thigh, a lower leg, a wrist joint, a knee joint, or the like. The term "imaging direction" refers to a general direction of the subject Obj in imaging, such as posterior-anterior (PA) or anterior-posterior (AP). The "other" imaging form refers to a general posture and/or shape of the subject Obj in imaging, such as standing or lying down.

The storage unit 32 stores one or a plurality of pieces of positioning data 35. The positioning data 35 is information for specifying the arrangement of the subject Obj with respect to the imaging unit 11. Specifically, the positioning data 35 three-dimensionally specifies the position, posture, and shape of the subject Obj in a case where the subject Obj is imaged using the imaging unit 11. The term "three-dimensionally specify" means to specify a relative relationship with a reference object in a case of imaging (here, the radiographic unit 14) in a three-dimensional space such as an imaging room in which the imaging unit 11 is located. In the present embodiment, since the medical imaging processing apparatus 12 cooperates with the imaging unit 11 which is a radiographic apparatus, the storage unit 32 stores information for three-dimensionally specifying the position, posture, and shape of the subject Obj with respect to the radiographic unit 14 as the positioning data 35.

The storage unit 32 stores the positioning data 35 for each subject Obj or for each imaging part of the subject Obj. For example, the storage unit 32 stores, as the positioning data 35, two types of information of positioning data of a wrist joint, which is one of imaging parts of the specific subject Obj, and positioning data of a knee joint, which is one of the other imaging parts of the subject Obj. Therefore, the medical imaging processing apparatus 12 can appropriately select and use the positioning data 35 related to the imaging to be performed by using the subject information and the imaging information acquired by the information acquisition unit 31.

The positioning data 35 is data relating to the subject Obj, data relating to another subject different from the subject Obj to be imaged, or schematic model data. The data relating to the subject Obj is data representing the arrangement of the subject Obj with respect to the imaging unit 11 (or an imaging apparatus of the same type as the imaging unit 11 (an apparatus that may have the same imaging form as the imaging unit 11)) in the past imaging. That is, the data relating to the subject Obj is information for specifying the position, posture, and shape of the subject Obj itself in the past imaging. The data relating to the other subject is information for specifying the position, posture, and shape, in the past imaging, of a person different from the subject Obj currently being imaged. The schematic model data is information for generally determining the ideal position, posture, and shape of the subject Obj, which is not related to actual imaging results of the specific subject, and is, for example, a three-dimensional model by computer graphics. The data related to the subject Obj and the data related to the other subject can be made into a three-dimensional model by computer graphics. In this case, although it is a three-dimensional model, data relating to the subject Obj and data relating to the other subject are used.

In the present embodiment, the positioning data 35 is data relating to the subject Obj, that is, information for specifying the position, posture, and shape of the subject Obj itself in the past imaging. This is to support the reproduction of the same position, posture, and shape as in the past imaging. In addition, in the present embodiment, the positioning data 35 is a three-dimensional model of the position, posture, and shape of the subject Obj in the past imaging (see FIG. 7).

In a case where the positioning data 35 is the data relating to another subject different from the subject Obj to be imaged or the schematic model data, the positioning can be appropriately supported even in a case where the subject Obj to be imaged has never imaged in the past, that is, in a case where the subject Obj is imaged for the first time. Therefore, in a case where the positioning data 35 is the data relating to the other subject, the storage unit 32 stores the positioning data relating to the other subject similar in shape and size to the subject Obj in association with the subject Obj. In addition, in a case where the positioning data 35 is the schematic model data, model data similar in shape and size to the subject Obj is stored in association with the subject Obj. The term "stored in association" means to make it possible to smoothly select, from among the plurality of pieces of positioning data 35, data having high relevance such as being similar in shape and size to the subject Obj by using the subject information and/or the imaging information of the subject Obj to be imaged.

In a case where the subject Obj is imaged using the imaging unit 11, the display unit 33 three-dimensionally displays the arrangement of the subject with respect to the imaging unit 11 by using the positioning data 35. Specifically, the display unit 33 displays the arrangement of the subject Obj with respect to the imaging unit 11 in a mode showing the three-dimensional position, posture, and shape of the subject Obj. As a result, the display unit 33 guides the user 25 to arrange the subject Obj as a target of the positioning.

The mode showing the three-dimensional position means a mode in which the user 25 can recognize a position where the subject Obj is to be arranged with respect to the imaging unit 11 from the display contents of the display unit 33. The mode showing the three-dimensional posture means a mode in which the user 25 can recognize a relative posture to be taken by the subject Obj with respect to the imaging unit 11 from the display contents of the display unit 33. The mode showing the three-dimensional shape means a mode in which the user 25 can recognize a specific three-dimensional shape (for example, an overall shape such as a bending angle of a joint) to be taken by the subject Obj from the display contents of the display unit 33. In particular, in the present embodiment, the display unit 33 displays the three-dimensional shape of the subject Obj in a mode that not only shows the overall shape but also shows the unevenness (such as the degree of muscle or fat sticking) of the subject Obj. This is to enable the user 25 to more accurately recognize the three-dimensional shape of the subject Obj.

The display unit 33 is, for example, a display (liquid crystal display device or the like) that displays, on a screen, a component that serves as a reference for positioning the subject Obj in the imaging unit 11 and the subject Obj, a projector that displays the arrangement of the subject Obj by projecting the arrangement of the subject Obj, or an augmented reality (AR) display that recognizes the arrangement of the subject Obj superimposed on reality. The AR display constituting the display unit 33 is, for example, a see-through type head-mounted display.

The camera 34 images a component (here, the radiographic unit 14) that at least serves as a reference in the positioning of the subject Obj in the imaging unit 11 and the subject Obj, by using visible light, infrared light, or the like. The video or image (hereinafter, referred to as a camera image) output by the camera 34 may be used by the display unit 33 depending on its specific configuration. For example, in a case where the display unit 33 is a liquid crystal display device, the display unit 33 displays the camera image and displays the arrangement of the subject Obj with respect to the imaging unit 11 by superimposing it on the camera image.

Figure 3:
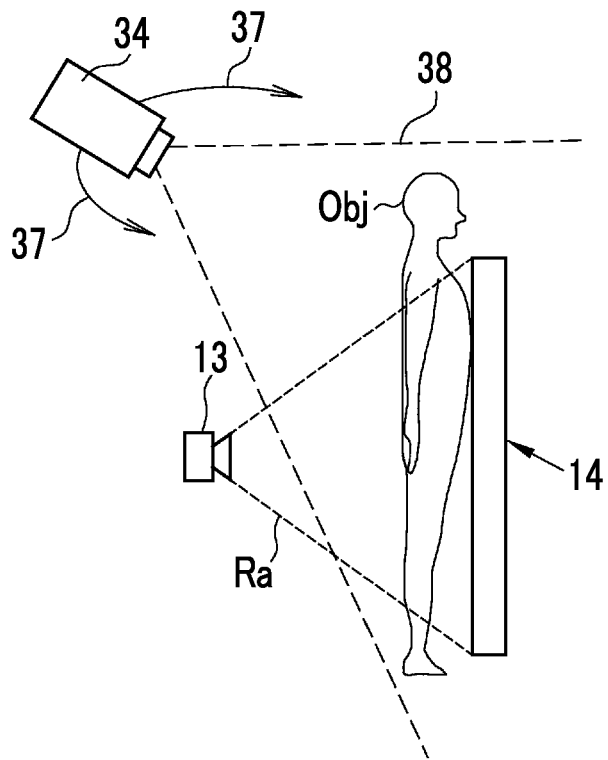
FIG. 3 is an explanatory view showing a camera constituting the medical imaging processing apparatus.

In addition, as shown in FIG. 3, the camera 34 can move in, for example, a direction of an arrow 37 with respect to the imaging unit 11, and can image the imaging unit 11 and the subject Obj from a plurality of directions while capturing the imaging unit 11 and the subject Obj in an imaging range 38. In a case where the imaging direction of the camera 34 is changed, the orientations of the imaging unit 11 and the subject Obj in the camera image are changed. Therefore, the display unit 33 adjusts the display of the arrangement of the subject Obj in accordance with the orientation of the imaging unit 11 captured in the camera image.

Figure 4:
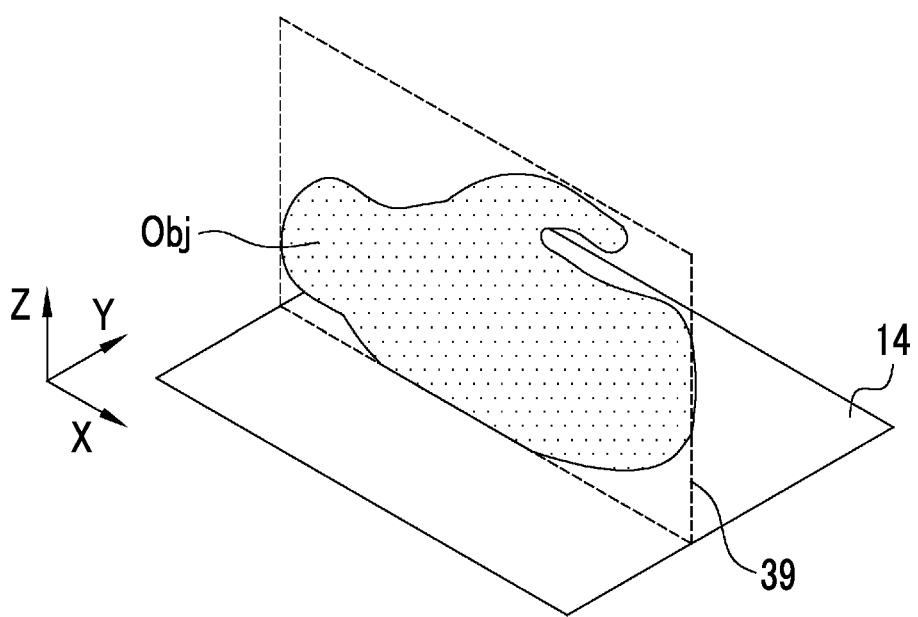
FIG. 4 is an explanatory view showing ideal arrangement of a wrist joint with respect to a radiographic unit.

Hereinafter, the operations of the medical imaging system 10 and the medical imaging processing apparatus 12 configured as described above will be described. As shown in FIG. 4, it is assumed that, for example, the subject Obj is a wrist joint and a radiation image of the side surface of the wrist joint is obtained. In this case, the subject Obj is usually arranged to be inclined at an angle of about 7 degrees with respect to the radiographic unit 14. Assuming that an X direction is a direction along the side of the radiographic unit 14 that directs the longitudinal direction of the subject Obj, a Y direction is a direction along the side of the radiographic unit 14 perpendicular to the X direction, and a Z direction is a direction perpendicular to the X direction and the Y direction (normal direction of the radiographic unit 14), it is ideal arrangement of the subject Obj that a plane 39 on which the subject Obj is shown for convenience is inclined at an angle of about 7 degrees in the Y direction with respect to the normal line (not shown) of the radiographic unit 14.

This is because in a case where the inclination is ±5 degrees or more with the angle as a reference, the obtained radiation image of the side surface of the wrist joint is treated as an imaging failure (so-called imaging loss) and re-imaging is required. In addition, in a case where the same subject Obj has been imaged in the past, since the imaging is also performed in the past imaging as described above, it is necessary to comply with the above reference in order to properly perform comparison with the radiation image obtained in the past imaging. Further, it is desirable that the newly captured radiation image is taken in the same position, posture, and shape as possible as in the past, within a range where imaging loss is not caused. This is to enable particularly accurate comparison with the radiation image obtained in the past imaging.

Figure 5:
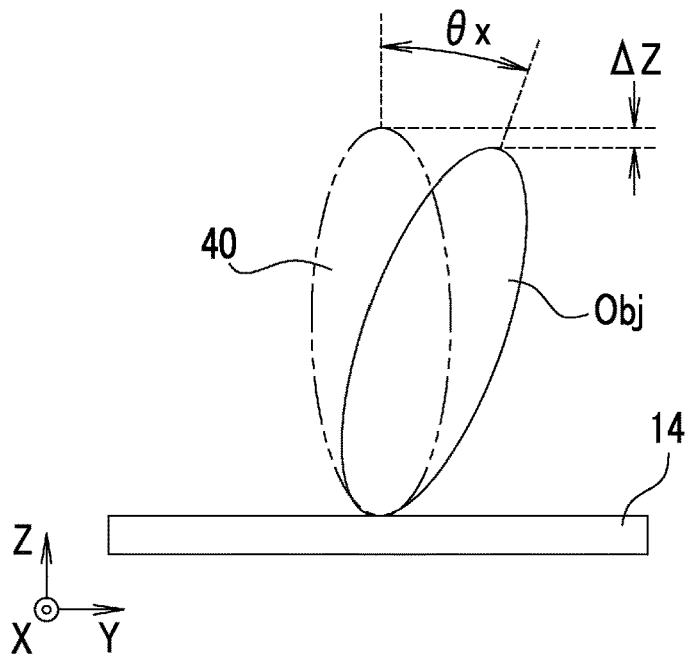
FIG. 5 is an explanatory view showing inclination of the wrist joint with respect to the radiographic unit.

However, in a case where the subject Obj is actually positioned, the subject Obj may deviate from the ideal arrangement. For example, as shown in FIG. 5, in a case of being viewed from the X direction, the actual subject Obj may deviate by an angle $\theta x$ (degrees) around the X direction with ideal arrangement 40 of the subject Obj as a reference. In a case where the angle $\theta x$ is large and the subject Obj is largely inclined from the ideal arrangement 40 to such an extent that the imaging loss is obvious, the positioning directionality of the subject Obj is clear. However, as described above, since the allowable inclination is as small as less than ±5 degrees from the ideal arrangement 40, it is difficult to make a determination on the accuracy of positioning (hereinafter, referred to as positioning determination) as to whether the imaging loss is caused or whether a radiation image that can be compared with the radiation image captured in the past can be obtained, in a case where the subject Obj is positioned with a certain degree of accuracy and the angle $\theta x$ is relatively small. In particular, in a case where the subject Obj is viewed from the Y direction, a difference $\Delta Z$ in height (length in the Z direction) between the ideal arrangement 40 and the actual subject Obj is hardly recognized in a case where the angle $\theta x$ is relatively small. Therefore, it is difficult to determine the positioning even in a case where the subject Obj is viewed from the Y direction.

Figure 6:
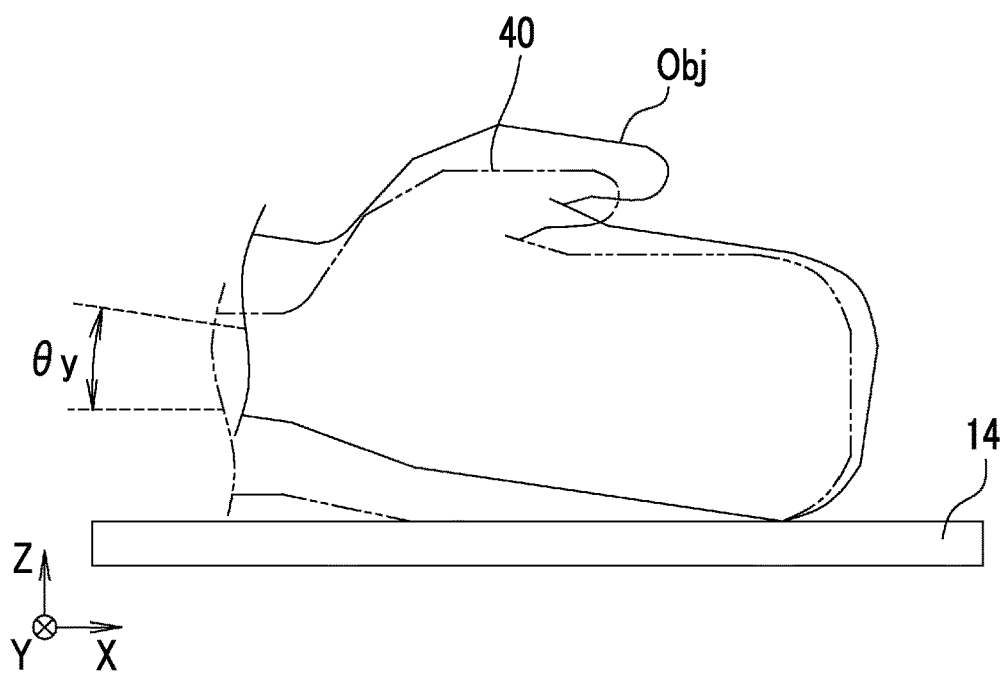
FIG. 6 is an explanatory view showing inclination of the wrist joint with respect to the radiographic unit in a case of being viewed from another direction.

In addition, as shown in FIG. 6, an ulnar side of a palm of the subject Obj is attached to the radiographic unit 14, but the actual subject Obj may be rotated in the Y direction from the ideal arrangement 40 depending on the pressing force thereof or the like. An angle $\theta y$ (degrees) of rotation around the Y direction also causes imaging loss and the like. In a case where the subject Obj is positioned with a certain degree of accuracy and the angle $\theta y$ is relatively small, the positioning determination is difficult, and in particular, the positioning determination regarding the angle $\theta y$ is difficult even in a case of being viewed from the X direction.

Figure 7:
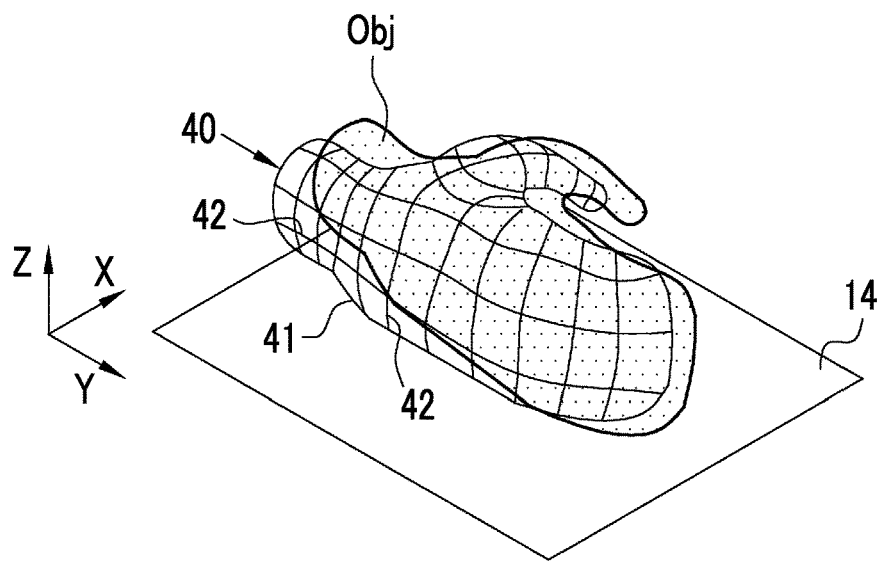
FIG. 7 is an explanatory view showing a display form for supporting arrangement of a subject.

Therefore, as shown in FIG. 7, the medical imaging system 10 and the medical imaging processing apparatus 12 three-dimensionally display, on the display unit 33, the ideal arrangement 40 of the subject Obj with respect to the radiographic unit 14 that serves as a reference for positioning in the imaging unit 11 by using the positioning data 35. According to the arrangement support display by the display unit 33, the user 25 can accurately grasp the position, posture, and shape in which the subject Obj is to be arranged at a glance. That is, according to the arrangement support display of the display unit 33, not only perception of any one of the position, the posture, or the shape in which the subject Obj is to be arranged but also comprehensive perception of these can be made. As a result, even after the subject Obj is positioned with a certain degree of accuracy, the positioning determination can be performed accurately and the subject Obj can be easily positioned in the ideal arrangement 40.

For example, in consideration of a case where the ideal arrangement 40 of the subject Obj is shown by two-dimensional (planar) display in which a contour 41 of the ideal arrangement 40 is superimposed on the subject Obj viewed from the X direction and the Y direction as in the related art, the subject Obj may deviate from the ideal arrangement 40 in a case of being viewed from the Y direction after positioning the subject Obj closer to the ideal arrangement 40 in a case of being viewed from the X direction. Then, in consideration of this point, after positioning the subject Obj closer to the ideal arrangement 40 in a case of being viewed from the Y direction, the subject Obj may deviate from the ideal arrangement 40 in a case of being viewed from the X direction again. Therefore, in the two-dimensional presentation method of the ideal arrangement 40 in the related art, it is not easy to accurately position the subject Obj even though information is included enough to perceive the ideal arrangement 40. On the other hand, according to the three-dimensional display of the ideal arrangement 40 on the display unit 33 of the medical imaging system 10 and the medical imaging processing apparatus 12, the position, posture, and shape in which the subject Obj is to be arranged can be comprehensively recognized without individually being aware of a plurality of parameters relating to positioning, such as the angle θx and the angle θy. Therefore, by positioning the subject Obj by viewing the arrangement support display of the display unit 33, accurate and easy positioning of the subject Obj can be supported.

The arrangement support display of the display unit 33 shows not only the contour 41 of the subject Obj in the ideal arrangement 40 but also the unevenness thereof by a wire frame 42. Therefore, it is easy to recognize the position, posture, and shape particularly accurately. As a result, the subject Obj can be positioned in the ideal arrangement 40 particularly easily and accurately.

Figure 8:
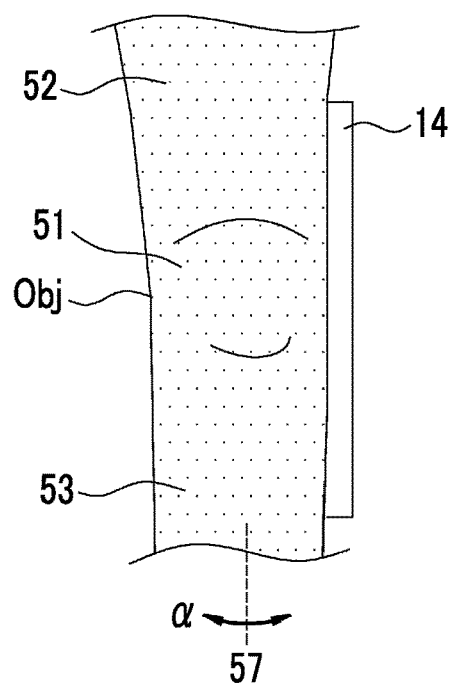
FIG. 8 is an explanatory view showing inclination of a knee joint with respect to the radiographic unit.

In the first embodiment, a case where the subject Obj is a wrist joint is taken as an example, but the subject Obj is optional. For example, as shown in FIG. 8, a knee joint can be the subject Obj. Then, according to the arrangement support display for three-dimensionally displaying the ideal arrangement 40 of the display unit 33, even in a case where the subject Obj is a knee joint, the position, posture, and shape in which the subject Obj is to be arranged can be comprehensively recognized. Specifically, in a case where the subject Obj is a knee joint and a radiation image of the side surface of the knee joint is captured (FIG. 8), the radiation image is captured by making not only a knee joint portion 51 but also a thigh 52 and a lower leg 53 continuing in front of and behind the knee joint portion 51 abut on the radiographic unit 14. In a case where the subject Obj is positioned in this manner, for example, rotation (twisting) of the knee joint portion 51, the thigh 52, and/or the lower leg 53 occurs around an axis 57 parallel to the side of the radiographic unit 14 depending on the manner in which the body weight is placed or the degree of force. That is, an angle α of rotation around the axis 57 is one of parameters for determining the success or failure of positioning.

Figure 9:
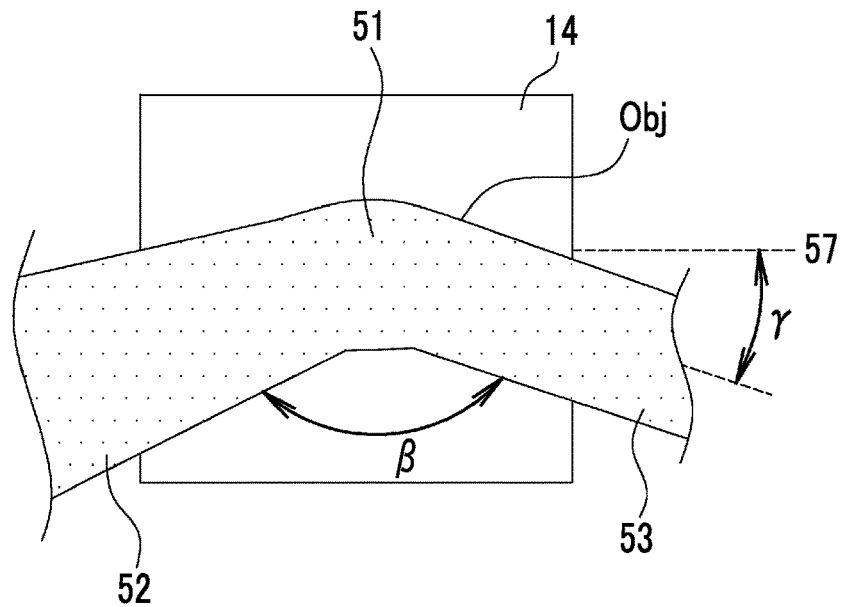
FIG. 9 is an explanatory view showing another parameter relating to arrangement of the knee joint.

As shown in FIG. 9, since a positional relationship between a bone and a cartilage of the knee joint portion 51 changes depending on an angle β formed by the thigh 52 and the lower leg 53, the angle β is also one of the parameters for determining the success or failure of positioning of the subject Obj. Further, since the lower leg 53 is usually imaged in parallel to the side of the radiographic unit 14, an angle γ formed by the lower leg 53 and the axis 57 parallel to the side of the radiographic unit 14 is also a parameter for determining the success or failure of positioning.

In a case where the subject Obj is a knee joint, a plurality of parameters such as the angle α, the angle β, and the angle γ need to be considered in the positioning as described above, but the accurate grasp thereof is not easy. Therefore, as in the first embodiment, in a case where the ideal arrangement (not shown) for capturing a radiation image of the side surface of the knee joint is three-dimensionally displayed on the display unit 33, the position, posture, and shape in which the knee joint as the subject Obj is to be arranged can be comprehensively recognized without considering the plurality of parameters individually. As a result, the subject Obj can be positioned in its ideal arrangement easily and accurately. The same applies to joints other than the wrist joint and the knee joint, and other subject Obj.

In the first embodiment, the display unit 33 may display contour lines or the like in place of the wire frame 42 in the arrangement support display. In a case where the ideal arrangement 40 is displayed by a so-called solid model in place of the wire frame 42, the unevenness of the subject Obj can be shown by the color of the texture.

The positioning data 35 can include information for three-dimensionally specifying the position and posture of the radiation source 13 with respect to the radiographic unit 14. Similarly to the display of the ideal arrangement 40 of the subject Obj, the display unit 33 displays the ideal arrangement of the radiation source 13, thereby supporting the positioning of the radiation source 13.

Second Embodiment

Figure 10:
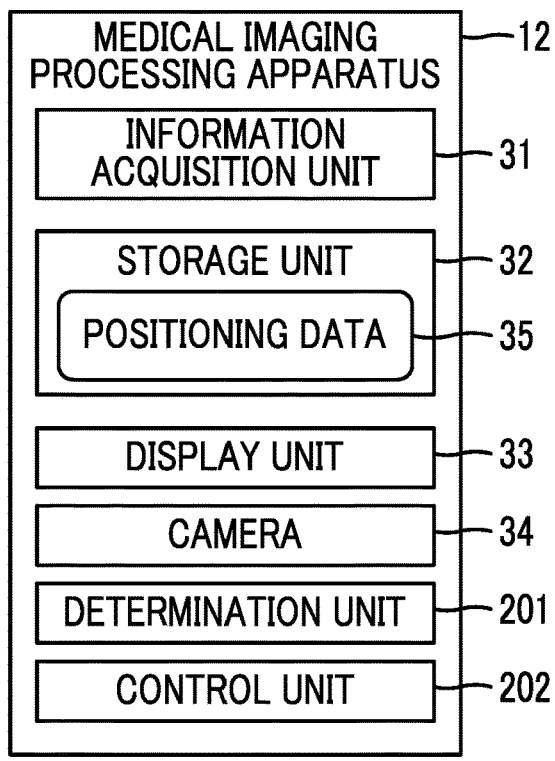
FIG. 10 is a block diagram showing a medical imaging processing apparatus including a determination unit and a control unit.

In the first embodiment, the arrangement support display is performed on the display unit 33 by using the positioning data 35, but the positioning data 35 can also be used for other controls. For example, as shown in FIG. 10, the medical imaging processing apparatus 12 may be provided with the determination unit 201 and the control unit 202.

The determination unit 201 determines a difference between the actual subject Obj and the ideal arrangement 40 of the subject Obj displayed by the display unit 33. The difference between the subject Obj and the ideal arrangement 40 is, for example, a distance between the corresponding parts of the subject Obj and the ideal arrangement 40 or an average thereof, an angle formed by the subject Obj and the ideal arrangement 40, or a volume of overlapping parts (or non-overlapping parts) between the subject Obj and the ideal arrangement 40. Therefore, the determination unit 201 determines the difference by using the distance, angle, and/or volume between the subject Obj and the ideal arrangement 40 of the subject Obj displayed by the display unit 33. The determination unit 201 can obtain the position, posture, and shape of the actual subject Obj by calculating, for example, the position, posture, and shape of the subject Obj using a plurality of camera images captured from different directions. In addition, the determination unit 201 can obtain the position, posture, and shape of the subject Obj in the ideal arrangement 40 from the positioning data 35 used by the display unit 33 for the arrangement support display. Therefore, the determination unit 201 can determine the difference. In addition, for example, the determination unit 201 compares the difference with a predetermined threshold value, and determines that "there is a difference" in a case where the difference is larger than the threshold value and the actual subject Obj and the ideal arrangement 40 deviate from each other.

In a case where the determination unit 201 determines that "there is a difference", the control unit 202 prohibits the imaging unit 11 from imaging the subject Obj. The term "prohibits imaging" means to forcibly prevent the execution of imaging even though the user 25 gives an instruction by measures such as interlocking the exposure to the radiation Ra.

As described above, the positioning data 35 can be used for determining the difference from the ideal arrangement 40. This determination simply and automatically performs the positioning determination performed by the user 25. Therefore, as described above, in a case where the difference is large as a result of the determination of the difference from the ideal arrangement 40 using the positioning data 35, the imaging loss can be reduced by prohibiting the imaging. As a result, it is possible to prevent useless exposure of the subject Obj due to re-imaging.

Third Embodiment

Figure 11:
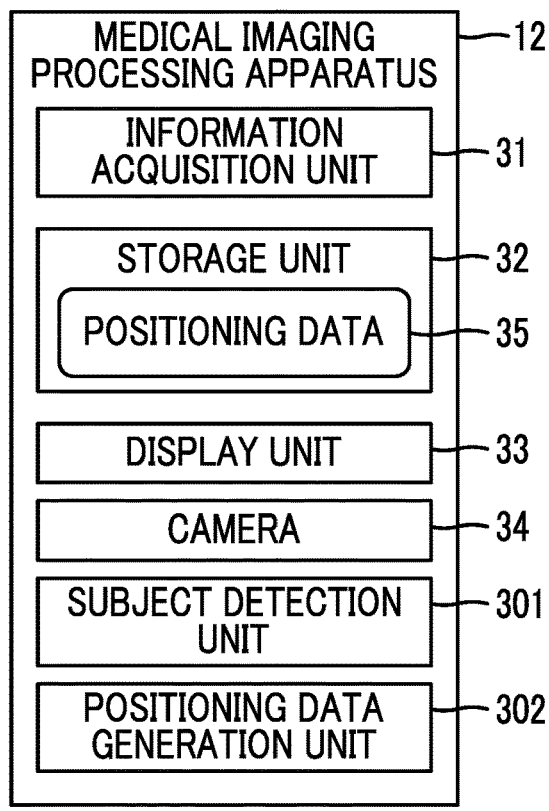
FIG. 11 is a block diagram showing a medical imaging processing apparatus including a positioning data generation unit.

In the first embodiment and the second embodiment, the storage unit 32 stores the positioning data 35, but the positioning data 35 can be generated by the medical imaging processing apparatus 12. In this case, as shown in FIG. 11, the medical imaging processing apparatus 12 comprises the subject detection unit 301 and the positioning data generation unit 302.

In a case where the subject Obj is imaged using the imaging unit 11, the subject detection unit 301 detects the subject Obj with respect to the imaging unit 11 from a plurality of locations. Detection of the subject Obj means obtaining the position, posture, and shape of the subject Obj with respect to the imaging unit 11, or an image or other information for specifying the position, posture, and shape. The subject detection unit 301 is, for example, any one or a combination of a camera for imaging, using visible light, infrared light, or the like, a component (here, the radiographic unit 14) that at least serves as a reference in the positioning of the subject Obj in the imaging unit 11 and the subject Obj, a pressure sensor provided on the imaging surface of the radiographic unit 14, a time-of-flight (TOF) camera for measuring a distance by the flight time of infrared light, and other instrument for measuring a distance or the like. The camera 34 can be used as the subject detection unit 301. In this case, the subject detection unit 301 and the camera 34 are identical.

The positioning data generation unit 302 generates the positioning data 35 using a result of the detection of the subject detection unit 301. For example, in a case where the positioning data 35 is data relating to the subject Obj and is a three-dimensional model, the positioning data generation unit 302 specifies the position, posture, and shape of each part of the subject Obj in a case where the imaging is successful, using an image or the like (camera image or the like) obtained from the subject detection unit 301, and generates a three-dimensional model thereof. Then, this data is associated with the subject information and the imaging information and stored in the storage unit 32 as the positioning data 35.

As described above, in a case where the medical imaging processing apparatus 12 itself generates the positioning data 35, it is not necessary to separately generate the positioning data 35 by a three-dimensional model creating device or the like, and the positioning data 35 can be automatically accumulated only by imaging the subject Obj using the imaging unit 11 cooperating with the medical imaging processing apparatus 12. As a result, a burden on the user 25 or the like in a case of creating the positioning data 35 can be reduced, and the medical imaging system 10 and the medical imaging processing apparatus 12 are favorable in usability.

Figure 12:
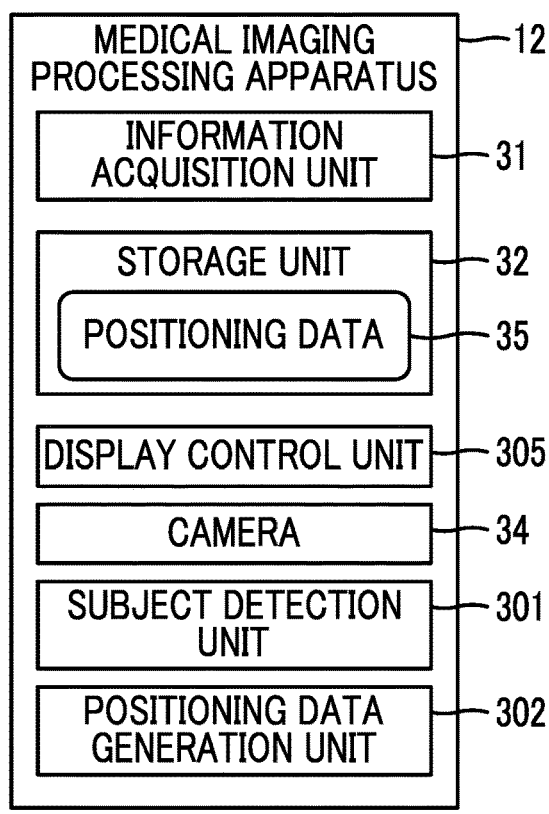
FIG. 12 is a block diagram showing a medical imaging processing apparatus including a display control unit.

In the first embodiment, the second embodiment, and the third embodiment, the medical imaging processing apparatus 12 includes the display unit 33 that three-dimensionally displays the ideal arrangement 40, but the medical imaging processing apparatus 12 can use a display or the like constituting another device or system as the display unit 33. In this case, as shown in FIG. 12, the medical imaging processing apparatus 12 can omit the display unit 33 and provide the display control unit 305 in place of the display unit 33. In a case where the subject Obj is imaged using the imaging unit 11, the display control unit 305 three-dimensionally displays the arrangement of the subject Obj with respect to the imaging unit 11 on a display unit constituting another device by using the positioning data 35. In this example, the display unit 33 of the medical imaging processing apparatus 12 of the third embodiment is replaced with the display control unit 305, thereby omitting the configuration of the display unit 33 from the medical imaging processing apparatus 12, but also in the medical imaging processing apparatus 12 of the first embodiment and the second embodiment, the display unit 33 can be omitted and the display control unit 305 can be provided.

In the first embodiment, the second embodiment, the third embodiment, and various modification examples, the medical imaging processing apparatus 12 includes the camera 34, but the medical imaging processing apparatus 12 can use a camera constituting another device or system as the camera 34. In this case, the configuration of the camera 34 can be omitted from the medical imaging processing apparatus 12 and replaced with a camera control unit (not shown) that controls a camera constituting another device or system, or a camera image acquisition unit (not shown) that acquires a camera image from a camera constituting another device or system. For example, in a case where the subject detection unit 301 is composed of the camera 34, the medical imaging processing apparatus 12 is preferably provided with a camera control unit that automatically moves the camera 34 to perform imaging from a plurality of locations and obtains a camera image necessary for generating the positioning data 35. This is because, by automatically obtaining the necessary camera image, the positioning data 35 can be automatically generated, and no explicit operation for generating the positioning data 35 is required. In particular, in a case where a camera and a display unit constituting another device or system are used, the configuration of the camera 34, the camera control unit, and the camera image acquisition unit can be omitted from the medical imaging processing apparatus 12. This is because another device or system performs these functions.

In the first embodiment, the second embodiment, the third embodiment, and various modification examples, the camera 34 is movable, but a plurality of cameras can be provided in place of making the camera 34 movable. In this case, among the plurality of cameras, the required camera is appropriately activated to capture a camera image.

The first embodiment, the second embodiment, the third embodiment, and various modification examples can be combined optionally (for example, partially) to constitute the medical imaging system 10 and the medical imaging processing apparatus 12.

In the above embodiment, for example, the hardware structure of a processing unit that executes various kinds of processing, such as the information acquisition unit 31, the determination unit 201, the control unit 202, the positioning data generation unit 302, and the display control unit 305, is various processors as shown below. The various processors include a central processing unit (CPU) that is a general-purpose processor that executes software (programs) to function as various processing units, a graphical processing unit (GPU), a programmable logic device (PLD) that is a processor capable of changing a circuit configuration after manufacture, such as a field programmable gate array (FPGA), and an exclusive electric circuit that is a processor having a circuit configuration exclusively designed to execute various kinds of processing.

One processing unit may be constituted by one of these various processors, or may be a combination of two or more processors of the same type or different types (for example, a plurality of FPGAs, a combination of a CPU and an FPGA, or a combination of a CPU and a GPU). In addition, a plurality of processing units may be constituted by one processor. As an example in which the plurality of processing units are constituted by one processor, first, as represented by a computer such as a client or a server, one processor is constituted by a combination of one or more CPUs and software and this processor functions as the plurality of processing units. Second, as represented by a system on chip (SoC) or the like, a processor that realizes the functions of the entire system including the plurality of processing units by using one integrated circuit (IC) chip is used. As described above, the various processing units are constituted by using one or more of the above-described various processors as the hardware structure.

Further, the hardware structure of these various processors is more specifically an electric circuit (circuitry) in a form in which circuit elements such as semiconductor elements are combined. In addition, the hardware structure of the storage unit is a storage device such as a hard disc drive (HDD) or a solid stage drive (SSD).

EXPLANATION OF REFERENCES

- 10: medical imaging system
- 11: imaging unit
- 12: medical imaging processing apparatus
- 13: radiation source
- 14: radiographic unit
- 20: console
- 21: display unit
- 22: operation unit
- 23: image generation unit
- 25: user
- 31: information acquisition unit
- 32: storage unit
- 33: display unit
- 34: camera
- 35: positioning data
- 37: arrow
- 38: imaging range
- 39: plane
- 40: ideal arrangement
- 41: contour
- 42: wire frame
- 51: knee joint portion
- 52: thigh
- 53: lower leg
- 57: axis
- 201: determination unit
- 202: control unit
- 301: subject detection unit
- 302: positioning data generation unit
- 305: display control unit

What is claimed is:

1. A medical imaging system comprising:
   an imaging device comprising a radiation source that generates a radiation for imaging and obtains a medical image or data used for generating the medical image by imaging a subject;
   a camera that photographs the imaging device and the subject and outputs a camera image;
   a processor configured to store positioning data for specifying an arrangement of the subject with respect to the imaging device; and
   a display device comprising a screen that three-dimensionally displays the arrangement of the subject with respect to the imaging device by using the positioning data in a case where the subject is imaged using the imaging device, wherein the camera is movable in a specific direction with respect to the imaging device as the specific direction is changeable, and
   the display device is configured to, in response to the specific direction having been changed, adjust displaying of the arrangement of the subject in accordance with an orientation of the imaging device captured in the camera image.

2. The medical imaging system according to claim 1, wherein the positioning data three-dimensionally specifies a position, a posture, and a shape of the subject.

3. The medical imaging system according to claim 1, wherein the positioning data is data relating to the subject, data relating to another subject different from the subject, or schematic model data.

4. The medical imaging system according to claim 3, wherein, in a case where the positioning data is the data relating to the subject, the positioning data is data representing the arrangement of the subject with respect to the imaging device in past imaging.

5. The medical imaging system according to claim 3, wherein the processor is further configured to store the positioning data relating to the other subject similar in shape and size to the subject in association with the subject in a case where the positioning data is the data relating to the other subject.

6. The medical imaging system according to claim 1, wherein the display device displays the arrangement of the subject in a mode showing a three-dimensional position, posture, and shape of the subject.

7. The medical imaging system according to claim 6, wherein the display device displays the three-dimensional shape of the subject in a mode showing unevenness of the subject.

8. The medical imaging system according to claim 1, wherein the processor is further configured to:
   determine a difference between the subject and the arrangement of the subject displayed by the display device, and
   prohibit the imaging device from imaging the subject in a case where determination is made that there is the difference.

9. The medical imaging system according to claim 8, wherein the processor is further configured to determine the difference by using a distance, an angle, or a volume between the subject and the arrangement of the subject displayed by the display device.

10. The medical imaging system according to claim 1, wherein the processor is further configured to:

detect the subject with respect to the imaging device from a plurality of locations in a case where the subject is imaged using the imaging device, and generate the positioning data by using a result of the detection.

11. A medical imaging processing apparatus comprising:

an imaging device comprising a radiation source that generates a radiation for imaging and obtains a medical image or data used for generating the medical image by imaging a subject;

a camera that photographs a radiographic unit and the subject and outputs a camera image;

a processor configured to:

store positioning data for specifying an arrangement of the subject with respect to the imaging device by using the positioning data in a case where the subject is imaged using the imaging device, and a display device comprising a screen that three-dimensionally displays the arrangement of the subject with respect to the imaging device by using the positioning data in a case where the subject is imaged using the imaging device, wherein the camera is movable in a specific direction with respect to the imaging device as the specific direction is changeable, and the display device is configured to, in response to the specific direction having been changed, adjust displaying of the arrangement of the subject in accordance with an orientation of the imaging device captured in the camera image.

\* \* \* \* \*